| United States Patent [19] | [11] 3,975,235 |
| --- | --- |
| Niwa et al. | [45] Aug. 17, 1976 |

[54] PROCESS FOR THE PRODUCTION OF CEPHAMYCIN TYPE ANTIBIOTIC SUBSTANCES

[75] Inventors: Tomizo Niwa, Yokohama; Hitoshi Goi, Kawasaki; Takashi Shomura, Yokohama; Yasuaki Ogawa, Yokohama; Shigeharu Inouye, Yokohama, all of Japan; Kazuo Saito, deceased, late of Fujisawa, Japan, by Nobuko Saito, heir; Taro Niida, Yokohama, Japan

[73] Assignee: Meiji Seika Kaisha, Ltd., Tokyo, Japan

[22] Filed: Feb. 24, 1975

[21] Appl. No.: 552,282

[30] Foreign Application Priority Data
Mar. 11, 1974  Japan.............................. 49-27261

[52] U.S. Cl................................. 195/29; 195/36 C
[51] Int. Cl.²........................................... C12D 9/00
[58] Field of Search................................. 195/29, 2

[56] References Cited
UNITED STATES PATENTS

| 3,801,458 | 4/1974 | Fildes et al. ........................ 195/29 |
| 3,862,004 | 1/1975 | Takahashi et al..................... 195/29 |

*Primary Examiner*—A. Louis Monacell
*Assistant Examiner*—Robert J. Warden
*Attorney, Agent, or Firm*—Flynn & Frishauf

[57] ABSTRACT

Novel 7-(5-amino-5-carboxyvaleramido)-7-methoxy-3-hydroxymethyl-3-cephem-4-carboxylic acid derivatives. Such derivatives are prepared by subjecting cephamycin type compounds to the action of esterase enzyme of mold fungi.

6 Claims, No Drawings

PROCESS FOR THE PRODUCTION OF CEPHAMYCIN TYPE ANTIBIOTIC SUBSTANCES

This invention relates to a new product and a new process for the production of cephamycin type antibiotics substances. Particularly, this invention relates to new products having the general formula (II) and a process for the production of 7-(5-amino-5-carboxyvaleramido)-7-methoxy-3-hydroxymethyl-3-cephem-4-carboxylic acid or its N-substituted derivative represented by the following general formula [II] and pharmaceutical acceptable salts thereof:

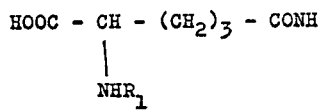

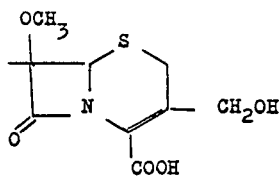

wherein $R_1$ represents hydrogen, a lower acyl group, an arylacyl group, a lower alkoxycarbonyl group or an arylalkoxycarbonyl group characterized in that a cephamycin type compound of the following general formula [I]:

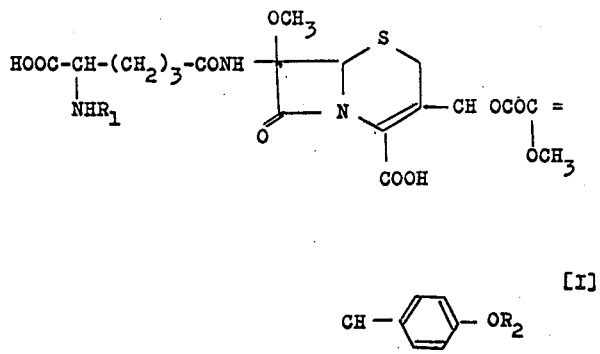

wherein $R_1$ has the same meanings as above and $R_2$ represents hydrogen, sulfo group, a lower acyl group or an arylalkoxycarbnyl group, is subjected to the action of esterase enzyme of mold fungi or a fermentation product containing esterase enzyme and, if necessary, the obtained free acid is converted into its salt or the salt is converted into free acid.

More specially, this invention relates to a process wherein cephamycin A (wherein $R_1 = H$, $R_2 = SO_3H$ in the above-mentioned general formula [I] and cephamycin B ($R_1 = R_2 = H$ in the general formula [I]) as well as their N,O-substituted or N-substituted derivatives ($R_1$ and/or $R_2$ have the same meanings as above, in the general formula [I]) are subjected to the action of the esterase enzyme (hereinafter referred to as esterase) capable of specifically acting upon said substances to produce 7-(5-amino-5-carboxyvaleramido)-7-methoxy-3-hydroxymethyl-3-cephem4-carboxylic acid ($R_1 = H$ in the above-mentioned general formula [II]) or its N-substituted derivative ($R_1$ has the same meanings as above, but excluding hydrogen in the general formula [II]) and the product so obtained is recovered.

In $R_1$ and $R_2$ of the above formulas (I) and (II) a lower acyl group means a lower acyl group having carbon atom 1–5 which may be substituted, for example, acetyl, propionyl, butyl, valeryl, an arylacyl group means acyl groups having phenyl, naphthyl or 5–6 membered heterocyclic radicals which may be substituted, for example benzoyl, toluyl, p-chlorobenzoyl, naphthoyl, niconinoyl, furoyl or thenoyl group, a lower alkoxycarbonyl group means a lower alkoxycarbonyl containing an alkyl having 1–4 carbon atoms, for example, methoxycarbonyl, acetoxycarbonyl, propoxycarbonyl or butoxycarbonyl, an arylalkoxycarbonyl group means phenyl- or naphthyl-methyloxycarbonyl, 5–6 membered heterocyclic radicals for example, furylmethyloxycarbonyl, thienylmethoxy carbonyl, pyridylmethoxycarbonyl.

As the most preferred examples of $R_1$ and $R_2$, there can be mentioned as follows: lower acyl radicals represent acetyl, propionyl, butyryl, pivaloyl and trichloroacetyl; arylacyl radicals represent benzoyl, p-chlorobenzoyl, isonicotinyl, phenylacetyl, phenoxyacetyl; lower alkoxycarbonyl radicals represent methoxycarbonyl, ethoxycarbonyl, n-butoxycarbonyl, chloropropoxycarbonyl; arylalkoxycarbonyl radicals represents carbobenzyloxy and the like.

A pharmaceutical acceptable salt means pharmaceutically acceptable alkali, alkali earth metal, for example sodium, calcium and the like and organic basic salt, for example, ammonium or triethylamine salts and the like.

7-(5-amino-5-carboxyvaleramido)-7-methoxy-3-hydroxymethyl-3-cephem-4-carboxylic acid or its N-substituted derivatives are important intermediates for the production of new and synthetic cephamycins and they are extremely difficult to be derived from cephamycins A and B or N,O-substituted derivatives thereof in a high yield through purely chemical procedures. For instance, by heating an aqueous solution of cephamycin B is formed a small amount of 7-(5-amino-5-carboxyvaleramido)-7-methoxy-3-hydroxymethyl-3-cephem-4-carboxylic acid, but the yield thereof is at best around 10 %.

As a result of our studies of a process for the simple production of the substance of the general formula [II] in a high yield from the cephamycin A or B which is easily obtainable according to the process of Japanese patent application No. 113999/1973, or from the O,N-substituted derivative of cephamycin B which is easily obtainable according to the process of Japanese patent application No. 116792/1973, it has been found that an esterase enzyme is present in some cultured broths of, for example, known molds such as *Aspergillus fumigatus*, Deposit number 2469 in the Fermentation Research Institute of the Agency of Industrial Science and Technology, Chiba, Japan, *Mucor lipoticus* Aac - 0102, Deposit number 566 in the Fermentation Research Institute of the Agency of Industrial Science and Technology and *Penicilium chrysogenum* IAM 7106. The enzyme is capable of specifically splitting the C-3 ester linkage of cephamycins A, B or N,O-substituted derivative thereof, and this invention has been completed upon this finding.

Though 7-(5-amino-5-carboxyvaleramido)-7-methoxy-3-hydroxymethyl-3-cephem-4-carboxylic acid, one of the compounds obtainable in this invention, is disclosed at page 126 of Japanese patent provisional publication No. 3286/1971 to be produced from a fermentation product, cephamycin C, through five chemical processes, it is obvious that the present process with enzymatic reaction is theoretically superior to the above process. The compounds of the general formula [II] which are producible according to the present invention are all new substances except for the above carboxylic acid.

The process of this invention may be conducted by reacting the starting material of the general formula [I] with an enzyme extract obtained from a cultured broth, its filtrate or fermentation product of a mold or a crude powder of esterase enzyme or a purified powder of the enzyme in a aqueous solution. And the molds which may be used in the present invention are well-known strains such as *Aspergillus fumigatus* (Deposit number 2469 in Fermentation Research Institute of the Agency of Industrial Science and Technology, Chiba-city, Japan), the known strain *Mucor lipoticus* Aac-0102 (Deposit number 566 in Fermentation Research Institute of the Agency of Industrial Sience and Technology, Chiba-city, Japan) and the known strain *Penicillium chrysogenum* IAM 7106 maintained in and available from Institute of Applied Microbiology of Tokyo University.

For the production of esterase enzyme by cultivation of the above-mentioned microorganism, there may be used various culture media commonly employed for the cultivation of a microorganism. More specifically, glucose, sucrose, glycerol, starch, oils used for cultivation and the like as a carbon source and peptone, bouillon, corn steep liquor, meat extract, fish meal, defatted soybean, wheat embryo, wheat bran and the like as a nitrogen source may be employed respectively and, if required, other additives such as inorganic salts, vitamins and the like may be employed in combination with the above.

As a cultivation method may be usually used submerged cultures such as shaking culture or agitated culture under aeration, but aerobic stationary culture or solid culture with wheat bran and so on may be also used as an efficient cultivation method. In cultivation, it is preferable to previously effect prepropagation on a small scale and then inoculate the so produced seed culture to a culture medium. Cultivation temperature may be optionally selected from the range of 20°–37°C, but a temperature of 25°–28°C is usually and preferably applied. Cultivation period is 3–10 days for effective production of the desired esterase.

Esterase is produced in a cultured broth in the case of a liquid culture and also obtained by easy extraction of a cultured broth with water or a suitable buffer solution in the case of a solid culture with wheat bran and the like.

The esterase contained in a cultured broth or its extract as such may be utilized in the present process without any further purification, but the esterase may be precipitated by the addition of an alcohol such as methanol, ethanol, isopropanol and so on or acetone, salted out with ammonium sulfate or dialyzed by dialysis or other means so as to be partially purified or concentrated and the so desalted enzyme solution may be treated by such means as freeze-drying so that the enzyme may be used in the form of a preparation of powder.

The esterase activity can be determined by the use of cephamycin A, B or ethoxycarbonylcephamycin B as a substrate. All the above-mentioned three substrates show antibacterial activities against Bacillus stearothermophylus and thus the esterase activity can be determined by reaction with these substrates and subsequent measurement of the reduction in their antibacterial activities by means of a bioassay method such as paper disc, etc. And, cephamycin B, where employed as a substrate, is reacted with esterase and then the reaction mixture is subjected to acidic extraction with ethyl acetate, whereby a fragment of esterase-decomposition products of the substrate, namely α-methoxy-p-hydroxycinnamic acid is easily transferred into the ethyl acetate layer and the ultraviolet absorption of the acid is measured to easily determine the esterase activity.

In carrying out the process of this invention, the reaction of hydrolysis of the cephamycins A, B and O,N-substituted derivatives thereof with esterase may be conducted as stated hereinbelow. A substrate concentration may vary depending upon the activity of the esterase applied and so on, but a range between 0.1 and 2% is suitable and a reaction pH is efficiently between 6.5 and 8.5, particularly around pH 7. A reaction temperature may be within 30°–60°C, but a temperature between 40° and 50°C is usually advantageous, since a higher temperature makes esterase inactive. And it is effective to provide the reaction mixture with suitable shaking or agitation during the reaction proceeding. A reaction period is preferable as short as possible, but a longer period is advantageous for complete proceeding of enzyme reaction and 4–50 hours is commercially proper after all. As an enzyme solution may be utilized a filtrate derived from liquid culture or an extract derived from solid culture, in which a suitable concentration of the substrate is dissolved for reaction, and, alternatively, a purified enzyme or a solid fermentation product containing the enzyme may be dissolved or suspended in a solution of the substrate. Also, it is expected as feasible to continuously use esterase in the form of a medium having the enzyme adsorbed thereon or in an insoluble state.

The modified substances from cephamycins of the general formula (II) which are produced according to the present process may be isolated from the reaction mixture and purified in the manner as summarized below.

In the purification of the 7-(5-amino-5-carboxyvaleramido)-7-methoxy-3-hydroxymethyl-3-cephem-4-carboxylic acid derived from the reaction mixture of cephamycins A or B treated with esterase, it is preferable to use an adsorption method using adsorbents such as an anion exchange resin, active charcoal and the like, since the present substance is a water-soluble acidic substance. For instance, the desired product in the reaction mixture is adsorbed on an anion exchange resin Dowex 1 × 2 (Cl-form) or DEAE-Sephadex A-25 (Cl-form), eluted with a suitable salt solution and then chromatographed over active charcoal, the procedures of which are effective means for the purification of the present substance. In the case of the compounds of the general formula [II] wherein $R_1$ is other than a hydrogen group, a organic solvent extraction method may also be effectively utilized in addition to the abovementioned utilization of ion exchange resins or active charcoal. More specifically, the enzymatic reaction mixture is adjusted with a mineral acid to pH 2–4 and extraction with ethyl acetate is effective to (first) remove α-methoxy-p-hydroxycinnamic acid and its derivatives. Further, the aqueous layer, as it is at pH 2–4, is extracted with n-butanol, whereby the desired product of this invention is extracted into the n-butanol layer. The n-butanol layer as such is concentrated to dryness to give the present compound in the form of a free acid or, after being transferred into an aqueous solution of sodium bicarbonate, the aqueous layer is concentrated to dryness to give the present compound in the form of its sodium salt. When transferred into an aqueous solution containing a base such as potassium bicarbonate, ammonia, triethylamine and the like, the desired compound of this invention may be in the form of the corresponding salt.

Morphological characteristics of *Apergillus fumigatus* (Deposit number 2469 in Fermentation Research Institute of the Agency of Industrial Science and Technology) which is one of the microorganisms used in this invention are as follows:

1. Growth on agar media

On malt extract-agar medium, potato-glucose-agar medium and Czapek's agar medium at 28°C., diameters (mm.) of the grown colonies are as shown below.

| Medium | 2 days | 3 days | 4 days |
| --- | --- | --- | --- |
| Malt extract-agar medium | 16 mm | 34 mm | 49 mm |
| Potato-glucose-agar medium | 19 | 35 | 47 |
| Czapek's agar medium | 11 | 23 | 33 |

On malt extract-agar medium, colonies are flocculent and surfaces are green to dark green. Reverse of colonies are colorless to pale yellow, no particular coloring being observed.

Morphological properties

When observed on the above media under a microscope, conidial heads are cylindrical in shape and have tight conidia. Conidiophores are short and smooth and ended with flask-like vesicle. Sterigmata are single on the upper half of vesicle. Conidia are spherical, of a diameter 2.5–4 μ and spiny throughout the surface.

2. Physiological properties

Relationships between the growth diameters (mm) of colonies on malt extract-agar medium and the growth conditions (pH, temperatures) are as shown below.

| (1) pH (at 28°C.) | | | |
| --- | --- | --- | --- |
| pH | 2 days | 3 days | 4 days |
| 5.0 | 16 mm | 32 mm | 44 mm |
| 7.0 | 16 | 34 | 49 |
| 9.0 | 14 | 27 | 40 |

| (2) Temperatures (at pH 7.0) | | | | |
| --- | --- | --- | --- | --- |
| Temp. | 2 days | 3 days | 4 days | 12 days |
| 15°C | 0 | 0 | 0 | 16 mm |
| 28°C | 16 | 34 | 49 | — |
| 37°C | 38 | 65 | 78 | — |

3. Utilization of carbon sources

Utilization of carbon sources on czapek's medium.

Positive: Glucose, starch, sucrose, mannose, galactose, arabinose, xylose, fructose, dextrin Negative: cellulose From the above morphological characteristics, this strain has been proved to belong to the genus *Aspergillus* and to *Aspergillus fumigatus*, as compared with well-known strains by "The genus Aspergillus" (1965): Raper & Fennel (Williams & Wilkins comp., Boltimore) (Further, this strain was identified by synchronous cultivation with *Aspergillus fumigatus* IFO 7079 as. type culture).

EXAMPLE 1

Each 100 ml portions of a liquid culture medium (pH 6.5) composed of 4 % soluble starch, 3 % defatted soybean meal, 0.3 % potassium primary phsphate and 0.3 % ammonium sulfate were taken into three 500 ml-volume Sakaguchi flasks. After sterilization in an autoclave at 120°C for 15 minutes, one platinum loop each of *Aspergillus fumigatus* (Deposit number 2469 in Fermentation Research Institute of Agency of Industrial Science and Technology), *Mucor lipolylicus* Aac - 0102 (Deposit number 566 in Fermentation Research Institute of Agency of Industrial Science and Technology) and *Penicilium chrysogenum* IAM 7106 on potato-glucose-agar slants was inoculated and then shaking culture was conducted at 28°C for 6 days in a reciprocal shaker to give a cultured broth of the respective microorganism.

On the other hand, 10 g. of wheat bran and 10 ml. of top water were mixed in each of three 500 ml-volume Erlenmeyer flasks. After sterilization in an autoclave at 120°C for 15 minutes, one platinum loop each of the above-mentioned three strains was inoculated and stationary culture was conducted at 28°C. for 8 days. The cultured broth was extracted with 60 ml of water per flask and filtered to give an extraction filtrate.

The cultured broth and extraction filtrate thus obtained were used as an enzyme solution. An aliquote of 1 ml. of each enzyme solution and an aliquote of 1 ml. of each substrate solution containing cephamycins A, B or each of their N,O-substituted derivatives at a concentration of (1,000 μg/ml.) were added and then the resulting mixture was adjusted to pH 7.0. The reaction was effected at 40°C. for 2 hours and thereafter a reduced antibacterial activity was measured by means of paper disc bioassay method using an assay plate of *Bacillus stearothermophylus* to determine the hydrolysis rate of esterase. The results in the following Table were obtained.

Hydrolysis rates (%) of cephamycins A, B and their N,O-substituted derivatives by some fungal esterases

| | Enzyme | Substrate A | B | C | D | E | F |
| --- | --- | --- | --- | --- | --- | --- | --- |
| Liquid culture filtrate | *Asperfillus fumigatus* (Deposit number 2469 in Fermentation Research Institute of Agency of Industrial Science and Technology) | 75 | 75 | 90 | 100 | 55 | 60 |
| | *Mucor lipolyticus* (Deposit number 566 in Fermentation Research Institute of Agency of Industrial Science and Technology) | 60 | 75 | 60 | 75 | 80 | 35 |
| | *Penicilium chrysogenum* IAM 7106 | 35 | 55 | / | 40 | / | / |
| | *Aspergillus fumigatus* (Deposit number 2469 in Fermentation Research Institute of Agency of Industrial Science and Technology) | 90 | 100 | 90 | 100 | 80 | 45 |
| | *Mucor lipolyticus* (Deposit number 566 in | | | | | | |

Hydrolysis rates (%) of cephamycins A, B and their N,O-substituted derivatives by some fungal esterases

| Enzyme | Substrate | | | | | |
|---|---|---|---|---|---|---|
| | A | B | C | D | E | F |
| Fermentation Research Institute of Agency of Industrial Science and Technology) | 70 | 100 | 50 | 100 | / | / |
| Penicilium chrysogenum IAM 7106 | 45 | 60 | 70 | 60 | / | / |

In the above Table, abbreviations A–F have the following meanings.
A: Cephamycin A
B: Cephamycin B
C: N-ethoxycarbonylcephamycin A
D: N,O-diethoxycarbonylcephamycin B
E: N,O-dipropionylcephamycin B
F: N,O-dibenzyloxycarbonylcephamycin B

EXAMPLE 2

Spores of *Aspergillus fumigatus* (Deposit number 2469 in Fermentation Research Institute Agency of Industrial Science and Technology) were inoculated to 500 ml. of a liquid culture medium (pH 6.5) composed of 4.0 % soluble starch, 3.0 % soybean meal, 0.3 % potassium of 4.0 % soluble starch, 3.0 % soybean meal, 0.3 % potassium primary phosphate and 0.3 % ammonium sulfate and the shaking culture was conducted at 25°C. for 48 hours. The cultured broth so obtained was again inoculated to 20 l. of the same medium in agar ferment or as above and cultivation under aeration and agitation was conducted at 25°C. for 96 hours. After cultivation, the cultured broth was filtered to give 12 l. of the filtrate. To the filtrate was added ammonium sulfate to 0.7 saturation with stirring and allowed to stand at 5°C. overnight. The precipitate thus formed was collected and dissolved in 500 ml. of tap water. Insolubles were filtered off and the resulting filtrate (600 ml.) was dialyzed against ap tap ar 5°C. for 24 hours by the use of Visking tube. The dialyzed liquid was used as an enzyme solution.

An amount of 5 g. of cephamycin B (a purity of 50 %) was dissolved in 1 l. of the enzyme solution (adjusted to pH 7.3) and the reaction was conducted at 45°C. for 6 hours. After completion of the reaction, the reaction mixture was decolored by passing through a column of a synthetic adsorbent Amberite XAD-2 (100 ml.) and the effluent was treated with a column of an anion exchange resin Dowex 1 × 2 (Cl-form) (50 ml.) to have the desired product adsorbed on the resin. After washing with water, the column was eluted with a 0.05 M aqueous solution of sodium chloride. The first 50 ml portion was discarded and the next 250 ml portion was passed through a column of active charcoal (20 ml) thereby the desired product being absorbed on the active charcoal. Then, the column was eluted with water and each 10 ml portions of eluate were collected. Fractions Nos. 5–15 were collected (160 ml.) and freeze-dried to give 770 mg. of 7-(5-amino-5-carboxyvaleramido)-7-methoxy-3-hydoxymethyl-3-cephem-4-carboxylic acid (Na salt) as white powders.

M.p. 165°–172°C., Analysis: C, 42.91%; H, 4.90%; N, 9.68%. Calculated for $C_{15}H_{20}N_3O_8SNa$: C, 42.35%, H, 4.71%; N, 9.88%.

EXAMPLE 3

Each 100 g. of wheat bran and an aliquot of 100 ml of water was taken in each four 2 L.-volume Erlenmeyer flasks and sterilized. *Aspergillus fumigatus* (Deposit number 2469 in Fermentation Research Institute of Agency of Industrial Science and Technology) was inoculated and the cultivation was conducted at 25°C. for 8 days. An aliquot of 600 ml. of tap water was added to each cultured flask to extract at room temperature. The resulting extract was collected and dialyzed against tap water at 5°C. overnight by the use of Visking tube and 2.1 l of the dialyzed liquid (pH 6.9) was obtained which may be employed as an enzyme solution. An amount of 1.7 g. of the N,O-diethoxycarbonylcephamycin B of a purity of about 20% prepared separately was dissolved in about 20 ml. of an aqueous solution of sodium bicarbonate (pH 7.2) and the resulting solution was added to 850 ml. of the above-mentioned enzyme solution. The reaction was effected with stirring at 45°C. for 4 hours. After completion of the reaction, the reaction mixture was adjusted to pH 3 with dilute hydrochloric acid and washed with 300 ml. of ethyl acetate to remove impurities. Thereafter, the aqueous layer, while maintained at pH 3, was extracted three times with 300 ml. of n-butanol, the extracts were combined and washed twice with a small amount of water. The n-butanol extract thus obtained was reextracted twice with 100 ml. of a dilute aqueous solution of sodium bicarbonate. The neutral aqueous extract was concentrated to dryness to give about 500 mg. of crude powders containing N-ethoxycarbonyl-7-(5-amino-5-carboxyvaleramido)-7-methoxy-3-hydroxymethyl-3-cephem-4-carboxylic acid sodium salt. The so obtained product was dissolved in 20 ml. of water, adsorbed on a column (1.6 × 19 cm) of DEAE-Sephadex A-25 (Cl-form), developed with 350 ml. of a 0.05 normal aqueous solution of sodium chloride and then with about 100 ml. of a 0.1N aqueous solution of sodium chloride, whereby the desired product being eluted. These fractions having ultraviolet absorption (about 100 ml.) were collected, adjusted to pH 3 with 1 normal hydrochloric acid and extracted three times with 50 ml. of n-butanol. The combined extracts were washed twice with a small amount of water, adjusted to pH 7.0 with 30 ml. of a dilute aqueous solution of sodium bicarbonate and reextracted. The resulting aqueous solution was concentrated to about 2 ml., developed over a column of Sephadex G - 10 (1 × 50 cm) with pouring water and those fractious having ultraviolet absorption were collected and concentrated to dryness to give 72 mg. of N-ethoxycarbonyl-7-(5-amino-5-carboxyvaleramido)-7-methoxy-3-hydroxymethyl-3-cephem-4-carboxylic acid sodium salt.

M.P. 130°–135°C., Analysis: C, 42.8%; H, 4.8%; N, 7.9%. Calculated for $C_{18}H_{24}N_3O_{10}SNa$: C, 43.5%; H, 4.9%; N, 8.4%.

(I) 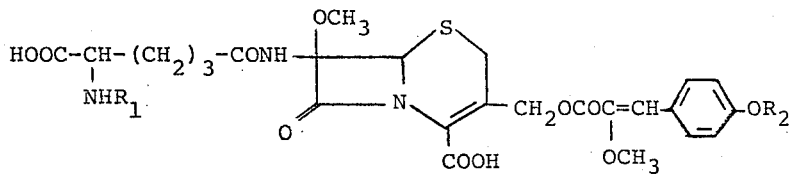

EXAMPLE 4

Following the same treatment procedures as in the Example 3 except that 1.6 g. of N,O-dibenzyloxycarbonylcephamycin B(a purity of 40%) was employed instead of the N,O-diethoxycarbonylcephamycin B, there was obtained 160 mg. of N-benzyloxycarbonyl-7(5-amino-5-carboxyvaleramido)-7-methoxy-3-hydroxymethyl-3-cephem-4-carboxylic acid soidum salt as powders.

M.P. 155°–160°C, Analysis: C, 49.0%, H, 4.8%; N, 7.3%. Calculated for $C_{23}H_{26}N_3O_{10}SNa$: C, 49.4%; H, 4.7%; N, 7.5%.

EXAMPLE 5

Following the same treatment procedures as in the Example 3 except that 1.3 g. of N,O-dipropionylcephamycin B (a purity of 20%) was employed instead of the N,O-diethoxycarbonylcephamycin B, there was obtained 50 mg. of N-propionyl-7-(5-amino-5-carboxyvaleramido)-7-methoxy-3-hydroxymethyl-3-cephem-4-carboxylic acid sodium salt as powders.

M.P. 145°–150°C. Analysis: C, 44.2%; H, 4.7%; N, 8.2%. Calculated for $C_{18}H_{24}N_3O_8SNa$: C, 44.9%; H, 5.0%; N, 8.7%.

What is claimed is:

1. A process for the production of 7-(5-amino-5-carboxyvaleramido)-7-methoxy-3-hydroxymethyl-3-cephem-4-carboxylic acid or its N-substituted derivative represented by the following formula (II) 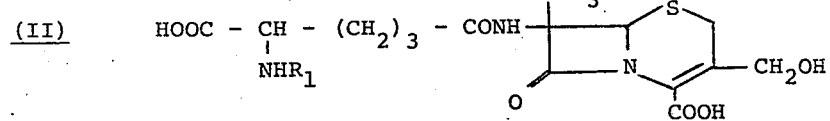

wherein $R_1$ represents hydrogen, a lower acyl group, and an arylacyl group, a lower alkoxycarbonyl group or an arylalkoxycarbonyl group characterized in that a cephamycin type compound of the following formula: wherein $R_1$ is defined as above and $R_2$ represents hydrogen, a sulfo group, a lowr acyl group or an arylalkoxycarbonyl group, is subjected to the action of an esterase enzyme capable of hydrolyzing an ester bond of said compound (I).

2. A process as claimed in claim 1, wherein the cephamycin compound (I) is selected from the group consisting of:
   1. cephamycin A
   2. cephamycin B
   3. N-Ethoxycarbonylcephamycin A
   4. N,O-diethoxycarbonylcephamycin B
   5. N,O-dipropionylcephamycin B and
   6. N,O-dibenzyloxycarbonylcephamycin B.

3. A process as claimed in claim 1, wherein the compound (II) is selected from the group consisting of:
   1. 7-(5-amino-5-carboxyvaleramido)-7-methoxy-3-hydroxymethyl-3-cephem-4-carboxylic acid,
   2. N-Ethoxycarbonyl-7-(5-amino-5-carboxyvaleramido)-7-methoxy-3-cephem-4-carboxylic acid,
   3. N-benzyloxycarbonyl-7-(5-amino-5-caboxyvaleramido)-7-methoxy-3-hydroxymethyl-3-cephem-4-carboxylic acid, and
   4. N-propionyl-7-(5-amino-5-caboxyvaleramido)-7-methoxy-3-hydroxymethyl-3-cephem-4-carboxylic acid.

4. A process as claimed in claim 1, wherein the esterase enzyme is in the form of:
   1. Aspergillus fumigatus, Deposit No. 2469,
   2. Mucor lipoticus Aac-0102, or
   3. Penicilium chrysogenum IAM 7106.

5. A process as claimed in claim 1, wherein the said cultivation is effected at a temperature of 30°C. to 60°C., at a value of pH 6.5 to 8.5, for 4-50 hours.

6. A process as claimed in claim 1 wherein the concentration of the said esteraze enzyme is about 0.1–2%.

* * * * *

UNITED STATES PATENT OFFICE
CERTIFICATE OF CORRECTION

PATENT NO. : 3,975,235
DATED : August 17, 1976
INVENTOR(S) : TOMIZO NIWA et al

It is certified that error appears in the above-identified patent and that said Letters Patent are hereby corrected as shown below:

Column 1, line 53: replace "arylalkoxycarbnyl" with
--- arylalkoxycarbonyl ---.

Column 4, line 61: replace "a organic" with
--- an organic ---.

Column 6, line 10: replace "Williams & Wilkins comp., Bol-" with --- Williams & Wilkins Corp., Bal- ---.

Column 7, line 36: replace "ap tap ar" with
--- tap water at ---.

Column 4, line 2, replace "Bacillus stearothermophylus" with
-- Bacillus stearothermophylus --.

Signed and Sealed this second Day of August 1977

[SEAL]

Attest:

RUTH C. MASON
Attesting Officer

C. MARSHALL DANN
Commissioner of Patents and Trademarks